(12) United States Patent
Fathallah

(10) Patent No.: US 6,685,692 B2
(45) Date of Patent: Feb. 3, 2004

(54) DRUG DELIVERY SYSTEM

(75) Inventor: Marwan A. Fathallah, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 60 days.

(21) Appl. No.: 09/802,076

(22) Filed: Mar. 8, 2001

(65) Prior Publication Data

US 2002/0128628 A1 Sep. 12, 2002

(51) Int. Cl.[7] .................. A61M 5/32; A61M 37/00
(52) U.S. Cl. .................. 604/411; 604/414; 604/88
(58) Field of Search .................. 604/411, 414, 604/415, 416, 86, 88; 141/329

(56) References Cited

U.S. PATENT DOCUMENTS

| | | | |
|---|---|---|---|
| 4,392,850 A | * | 7/1983 | Elias et al. .................. 604/244 |
| 4,392,851 A | * | 7/1983 | Elias .................. 604/244 |
| 4,410,321 A | | 10/1983 | Pearson et al. |
| 4,601,704 A | | 7/1986 | Larkin |
| 4,607,671 A | | 8/1986 | Aalto et al. |
| 4,614,267 A | | 9/1986 | Larkin |
| 4,676,775 A | | 6/1987 | Zolnierczyk et al. |
| 4,874,366 A | | 10/1989 | Zdeb et al. |
| 4,985,016 A | | 1/1991 | Theeuwes et al. |
| 5,199,947 A | * | 4/1993 | Lopez et al. .................. 604/284 |
| 5,201,705 A | | 4/1993 | Berglund et al. |
| 5,205,821 A | | 4/1993 | Kruger et al. |
| 5,385,546 A | | 1/1995 | Kriesel et al. |
| 5,385,547 A | * | 1/1995 | Wong et al. .................. 604/414 |
| 5,478,337 A | | 12/1995 | Okamoto et al. |
| 5,484,406 A | | 1/1996 | Wong et al. |
| 5,766,149 A | | 6/1998 | Kriesel et al. |
| 6,063,068 A | | 5/2000 | Fowles et al. |
| 6,090,091 A | | 7/2000 | Fowles et al. |
| 6,090,092 A | | 7/2000 | Fowles et al. |

FOREIGN PATENT DOCUMENTS

WO   WO 95/19195   7/1995

* cited by examiner

Primary Examiner—Alfred Basichas
(74) Attorney, Agent, or Firm—Beth A. Vrioni

(57) ABSTRACT

A drug delivery system stores a beneficial agent and mixes the beneficial agent with a component in a reservoir, the mixture to be delivered to a patient. A plunger in the drug delivery system delivers the beneficial agent to a reservoir containing a component, such as diluent. The beneficial agent and component are mixed in the reservoir and the mixture flows from the reservoir to an access port in the drug delivery device to an administration set or other device to be delivered to a patient.

20 Claims, 9 Drawing Sheets

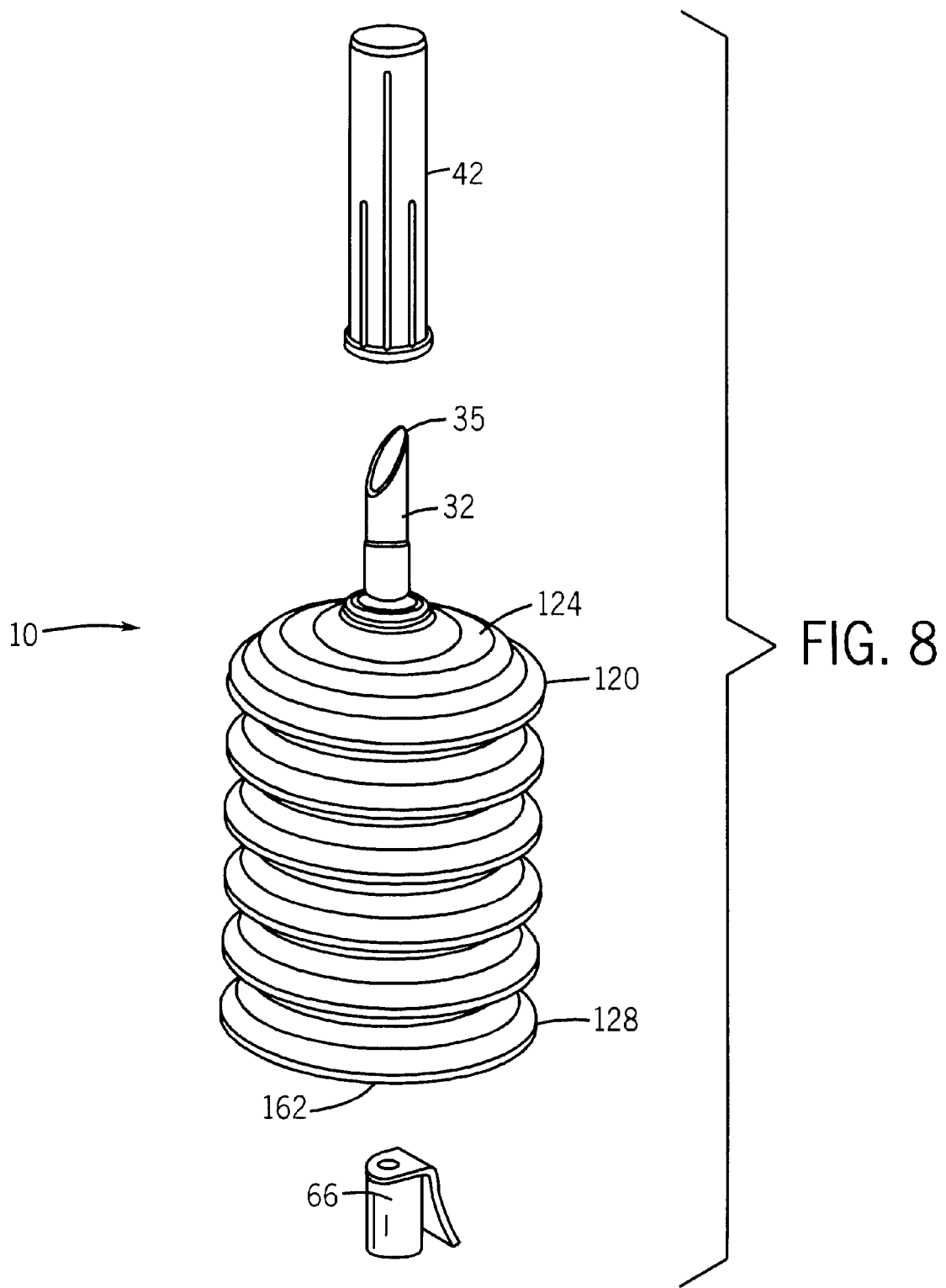

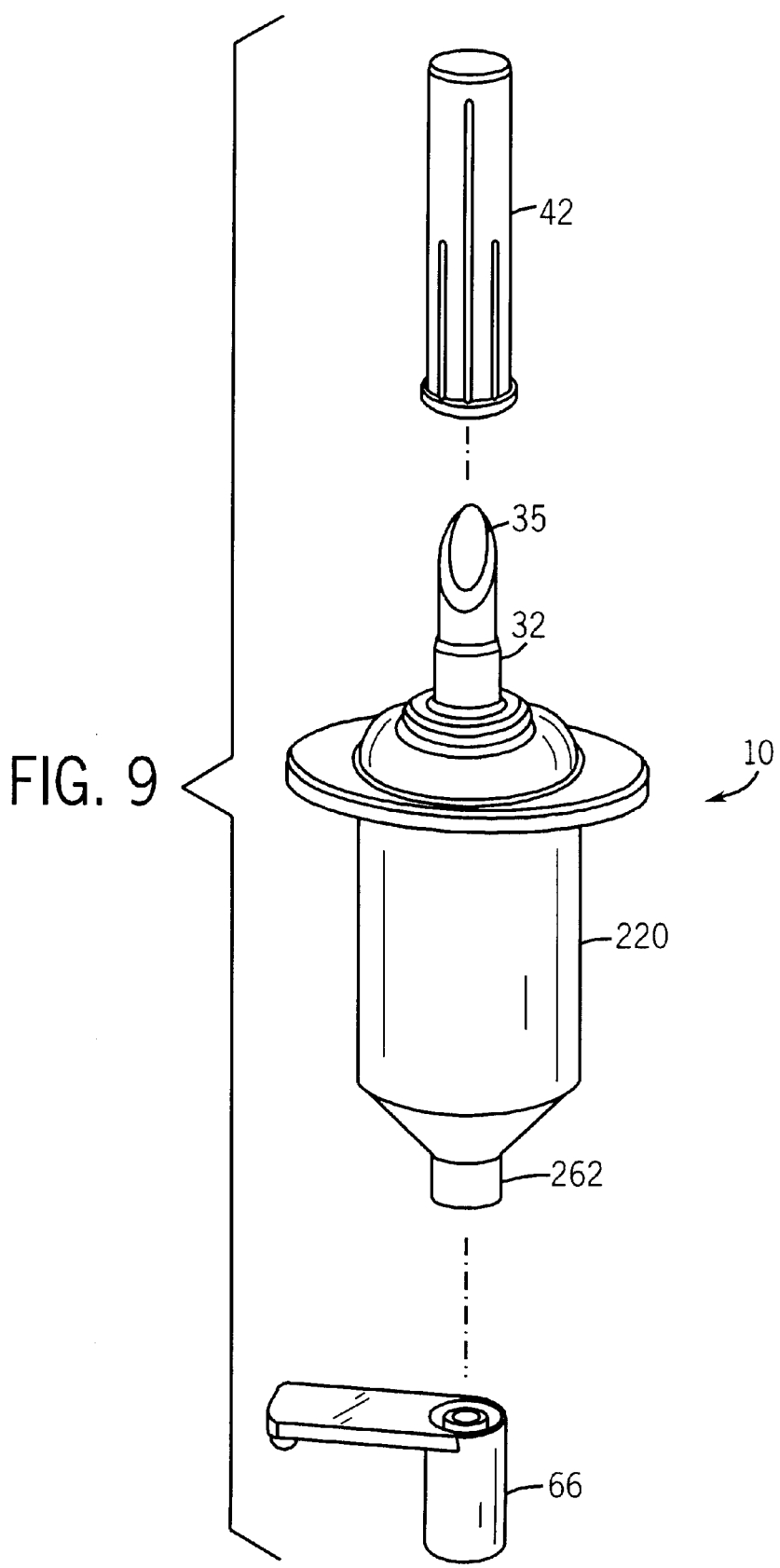

DRUG DELIVERY SYSTEM

FIELD OF THE INVENTION

The present invention relates to a drug delivery system. More particularly, the invention relates to a drug delivery system that stores a drug or other beneficial agent and subsequently delivers the drug to a reservoir containing a component and allows the drug and component mixture to flow from the reservoir through the drug delivery device to an administration set or other device to be delivered to a patient.

BACKGROUND OF THE INVENTION

Medicaments or drugs have been stored and delivered using several types of systems. In the past, many drug delivery devices were attached to a standard IV bag wherein the beneficial agent would mix with the diluent and then flow through an outlet port to an administration set. A common method of mixing a beneficial agent with a diluent is by adding the beneficial agent with a syringe through an additive port in a partial-fill diluent container. The beneficial agent and diluent was mixed by inverting the container, the resulting mixture delivered to the administration set through an outlet port in the diluent container.

Another example of a prior drug delivery device is disclosed in U.S. Pat. No. 4,614,267 to Larkin. Larkin discloses a drug delivery system comprising a stopper vial that attaches to a flexible container. In the Larkin system, the stopper is removed from the vial and the beneficial agent flows into the flexible container and then out an outlet port of the container to the patient.

An additional drug delivery device is described in U.S. Pat. No. 5,484,406 to Wong et al. Wong discloses a drug delivery device consisting of a drug container that is attached to a container including a diluent. The drug container is spiked providing fluid communication between the drug container and the diluent container. The drug and diluent are mixed in the diluent container, with the mixture flowing out a port of the diluent container to the patient In contrast, the present drug delivery device may be described as a flow through system with the drug and diluent flowing through the device to the administration set.

SUMMARY OF THE INVENTION

The present invention is a drug delivery system that provides a drug chamber for liquid, powder, or lyophilized drugs to be held in a stable formulation until it is administered to the patient. In addition to serving as the storage container for the beneficial agent, the present drug delivery system is also the vehicle for injecting the beneficial agent into a fluid reservoir to be administered to a patient. The present drug delivery device may be described as a flow through system with the drug and diluent flowing through the device to the administration set. In the present flow through system a beneficial agent is delivered to an external reservoir and mixed with a diluent before administering the beneficial agent and diluent mixture to a patient. An advantage of the present drug delivery system is that this system is compatible with standard IV containers (rigid or flexible) and standard administration sets.

Another advantage of the present flow-through drug delivery system is the elimination of non-delivered drug sitting in the drug delivery device. The present drug delivery system delivers the drug to a reservoir including a fluid, wherein the drug and fluid are mixed. After the drug and diluent are mixed, the mixture flows through the delivery system to the administration set, eliminating the disadvantage of drug dripping back into a delivery system without flowing to the administration set.

A further advantage of the present system is that the system provides both visual and audible evidence that the drug delivery system is activated. When the system is activated a stopper will make a popping noise as the stopper is released and the stopper plug will be located in the fluid reservoir. In addition, an automatic lock on the delivery system is triggered only after the entire drug is delivered to an external environment of the drug delivery system. Thus, the location of the plug in the reservoir, as well as the location of the base of the delivery device in a locked position, will allow the person administering the beneficial agent, and anyone checking the system later, to confirm that the drug has been delivered to the patient.

The present drug delivery system provides a totally contained and enclosed system for the beneficial agent. This contained system prevents unwanted exposure of the beneficial agent to the person administering the beneficial agent to the patient.

Moreover, the present drug delivery system reduces drug wastage by providing a device that may be connected to a standard IV bag without activation and delivery. If the present drug delivery system is connected to a standard IV without activation the beneficial agent need not be delivered immediately and may be available for use at a later time.

Furthermore, the present drug delivery system does not require needles to administer the drug to a standard IV system. A needleless system prevents the risk of transmission of various pathogens due to an inadvertent needle stick.

Additional advantages of the invention will be realized and attained by the apparatus and method particularly pointed out in the written description and claims hereof, as well as from the appended drawings. It is to be understood that both the foregoing general description and the following detailed description are exemplary and are intended to provide further explanation of the invention claimed.

BRIEF DESCRIPTION OF THE DRAWINGS

FIG. 8 is a perspective view of another embodiment of the drug delivery system of the present invention having a bellow container.

FIG. 9 is a perspective view of another embodiment of the drug delivery system of the present invention having a flexible container.

DETAILED DESCRIPTION

Figure 1:
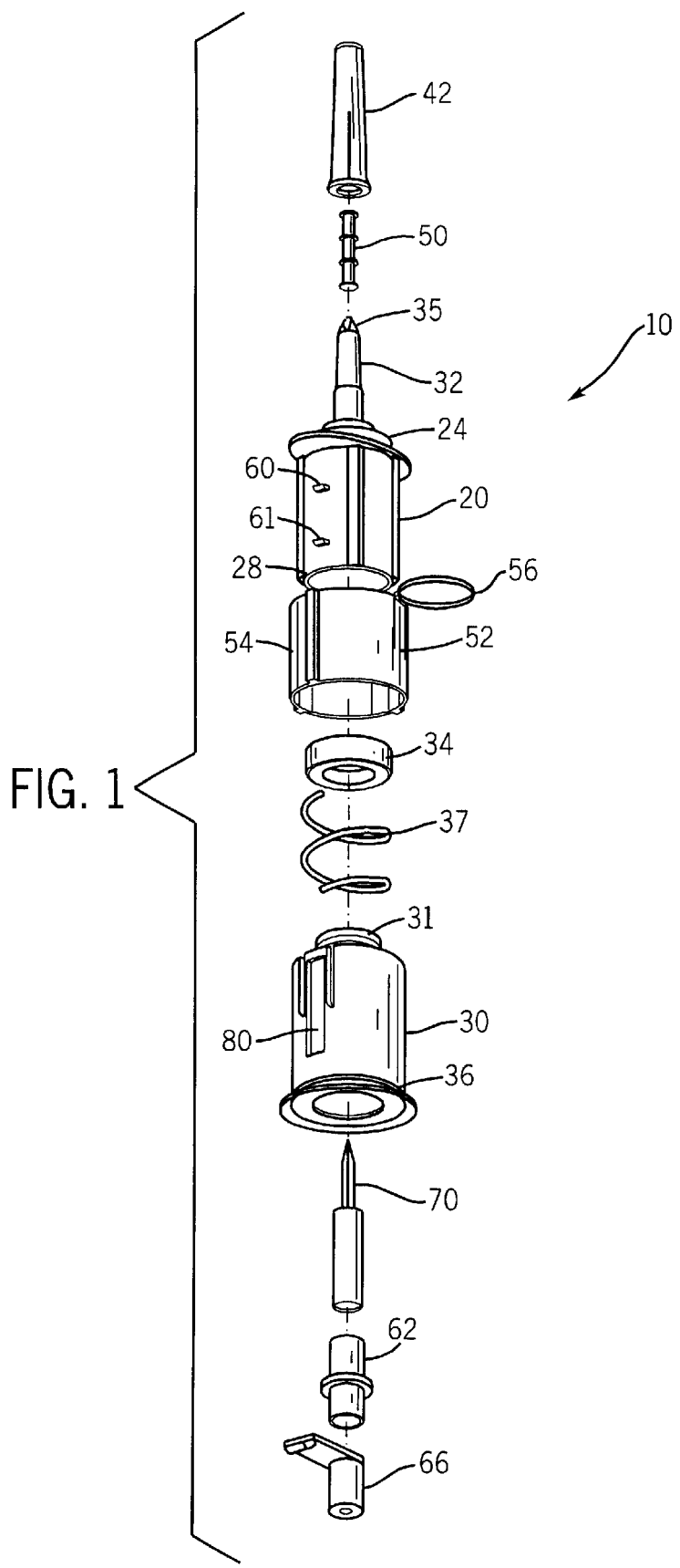
FIG. 1 is an exploded view of an embodiment of the drug delivery system of the present invention.
Figure 2A:
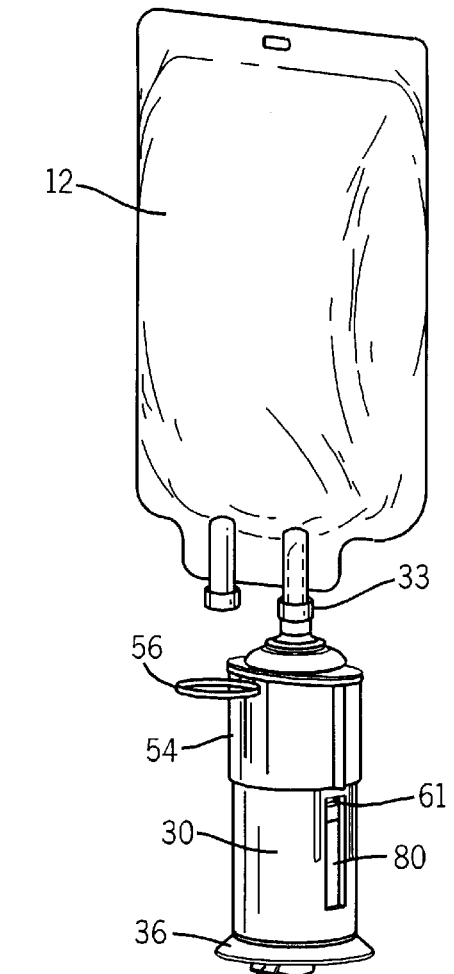
FIG. 2A is a perspective view of the drug delivery system illustrated in FIG. 1 connected with a standard IV bag.
Figure 2B:
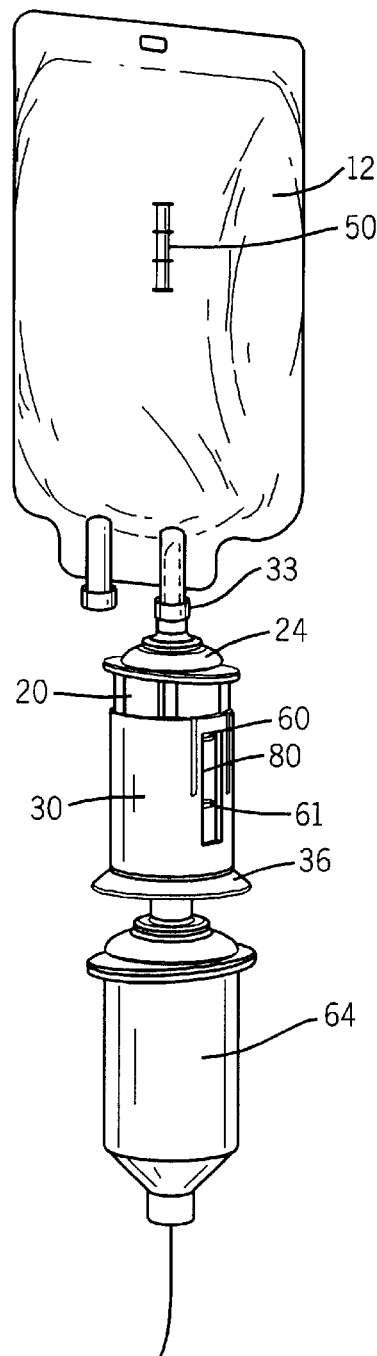
FIG. 2B is a perspective view of the drug delivery system illustrated in FIG. 1 activated and mated with a standard IV bag and administration set.
Figure 3:
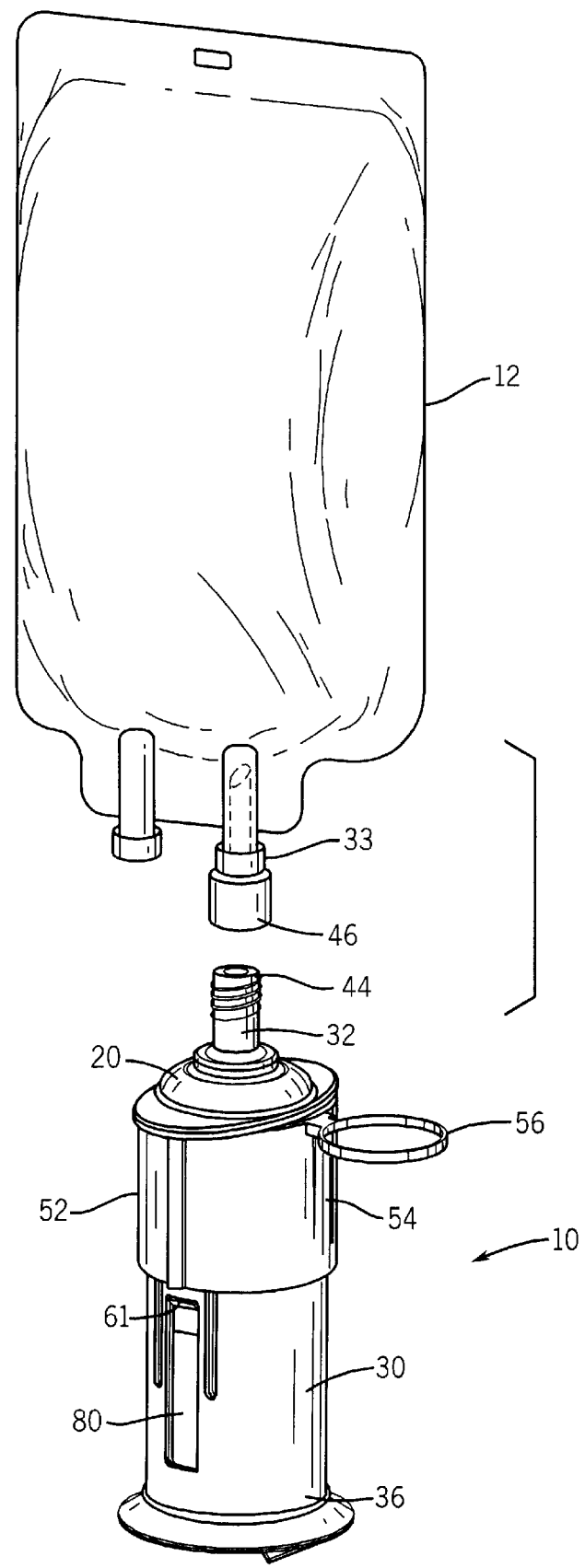
FIG. 3 is a perspective view of an embodiment of the drug delivery system of the present invention with male and female luer members attaching the drug delivery system to a standard IV bag.

The present invention is a drug delivery system, generally designated by the numeral 10. As shown in FIGS. 2A and 2B, the present drug delivery system 10 may be connected to a reservoir 12 containing a component, such as a diluent, that is mixed with a beneficial agent 14 before administering the mixture to a patient. The drug delivery system 10 as shown in FIG. 1 comprises a container 20 having an interior chamber 22, a first end 24, and a second end 28. The container 20 has a drug delivery tube 32 extending from the first end 24 of the container to provide a first flow path 21 for the beneficial agent from the container 20 to a reservoir 12, such as a standard part-fill IV bag or bottle. The reservoir may consist of any known container. In the preferred embodiment the drug delivery tube 32 includes a spike 35 that is inserted into a standard IV bag through an administration port 33 (see FIGS. 2A & 2B). However, the drug delivery tube 32 may be attached to the reservoir with other attachment means, such as male and female luer members 44, 46 (see FIG. 3). To maintain sterility a spike cover 42 may be attached to the spike 35 and removed prior to inserting the spike 35 into the standard bag.

Figure 4:
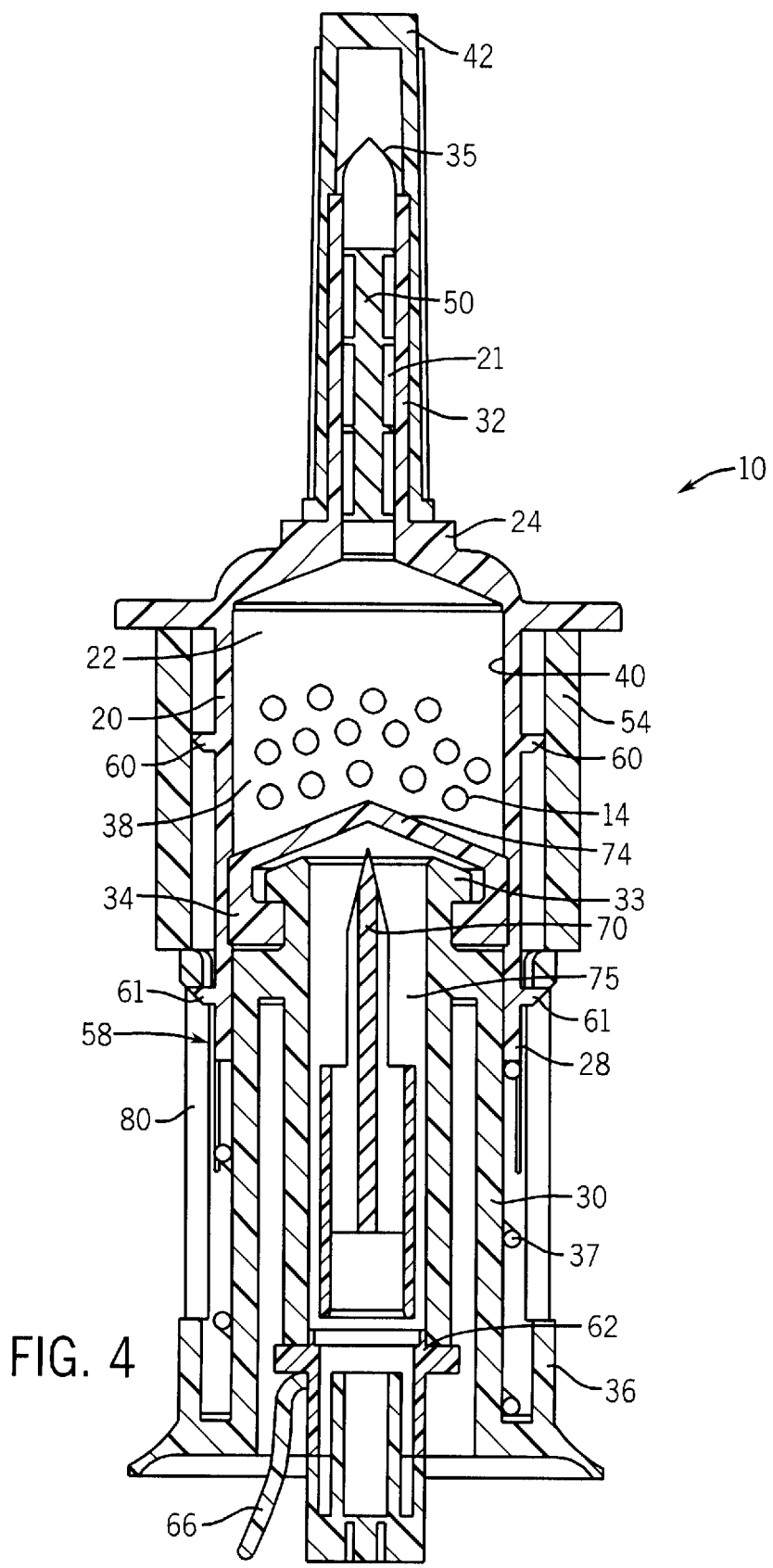
FIG. 4 is a cross-sectional view of the drug delivery system illustrated in FIG. 1.

The second end 28 of the container 20 is open and receives a plunger 30 (see FIG. 4). The plunger 30 comprises a first end 31 having a piston head 34 and a second end or base 36 opposite the piston head 34. Positioned about the plunger 30 is a spring 37 to bias the plunger 30 away from the first end 24 of the container 20. The piston head 34 slides within the interior chamber 22 of the container 20 along an inside surface 40, with the piston head 34 and the container 20 defining a drug chamber 38 for holding a beneficial agent or drug 14 to be delivered to a patient. The beneficial agent or drug 14 may be freeze-dried, liquid or a powdered drug to be held in a stable formulation until it is administered to the patient. The container 20 may be manufactured of glass, plastic, or other materials compatible with the beneficial agent, and may be a rigid, semi-rigid, or flexible structure.

In a preferred embodiment, the delivery tube 32 receives a rubber plug 50. The rubber plug 50 positioned within the delivery tube 32 provides a seal between the external environment and the drug chamber 38. The rubber plug or seal 50 may be fitted such that it is held in place within the delivery tube 32 by mere friction force. This rubber plug 50 serves as a visual and audible signal that the drug delivery system 10 has been activated which will be described below. Although the present configuration includes a rubber plug, clearly other components could be used to seal the drug chamber from the external environment and to indicate the activation of the system, such as a rupturable membrane or a valve.

In the preferred embodiment the plunger 30 comprises a piston head 34 that slides within the interior chamber 22 of the container 20 to push the beneficial agent or drug 14 out of the container 20 through the first end 24 and into the reservoir 12. To prevent accidental or premature delivery of the drug a safety ring 52 may be included in the drug delivery system 10. In the preferred embodiment, the safety ring 52 consists of a sleeve 54 wrapped around the container 20 and a tear ring or strip 56. The safety ring 52 prevents the plunger 30 from inadvertently advancing the beneficial agent 14 through the container 20. Prior to delivering the beneficial agent 14 the tear strip 56 is pulled to remove the safety ring 52, allowing the plunger head 34 to advance toward the first end 24 of the container 20. As an additional safety feature, in the preferred embodiment the drug delivery system includes a lock 58 for engaging with the plunger member 30. The lock 58 is configured such that the lock 58 is not triggered until the entire drug 14 has been delivered outside of the drug chamber 38. In the preferred embodiment, the lock 58 comprises a pair of upper tabs 60 and a pair of lower tabs 61 that extend from the outside surface of the container 20 and a slot 80 located along the plunger 30 for receiving the tabs 60, 61. During assembly of the present drug delivery system, the lower tabs 61 are positioned within the slot 80. The upper tabs 60 are received in the slot 80 only after substantially all the beneficial agent is delivered to the reservoir. The lock 58 could include a wide range of configurations and is not limited to the specific construction described herein.

The second end 36 of the plunger 30 includes an access port 62 providing fluid communication to an external environment, such as a standard administration set 64. However, the access port 62 could be located at positions on the drug delivery system other than the second end 36 of the plunger 30, including near the drug delivery tube 32. To further maintain sterility of the system, the access port 62 may include a sterile seal 66, which is removed before attaching the administration set 64 to the drug delivery system 10. The seal 66 in the preferred embodiment comprises a pull tab cover. In addition, the plunger 30 includes an internal penetrator 70 axially aligned with the access port 62. As an administration set 64 is attached to the access port 62, a spike 72 of the administration set 64 pushes the internal penetrator 70 through a pierceable member 74 located in the piston head 34 to create a second flow path 75 through the plunger 30 to the access port 62. In the preferred embodiment, the pierceable member 74 is made of rubber such that the penetrator 70 remains embedded within the pierceable member 74, providing tamper evidence that the drug delivery system 10 has been accessed. To aid the visual identification of the penetrator's location, the container may comprise a transparent material and the penetrator 70 may comprise a color different from the other components of the system. Clearly, this feature is optional and the color or transparency of the materials may vary. For transportation purposes, the entire drug delivery system 10 may be packaged in a foil wrap, pouch, box, or other packaging means.

During operation of the preferred embodiment of the present drug delivery system 10, first the spike cover 42 is removed from the spike 35. The spike 35 is inserted into an administration port 33 on a standard IV bag 12 (see FIG. 2A). At this point, the drug delivery system is connected to the IV bag, but the beneficial agent 14 has not been mixed with the diluent, which allows the beneficial agent to be available for use at a later time. When the drug is to be delivered, the tear ring 56 is pulled to remove the safety ring 52. The drug delivery system is then held like a syringe, pushing the base 36 of the plunger 30 towards the first end 24 of the container 20. This plunging action creates pressure on the rubber plug 50 and forces the rubber plug 50 out of the delivery tube 32 and into the reservoir 12. When the rubber plug 50 is released an audible popping noise is made, creating an audible signal that the system has been activated.

Figure 5:
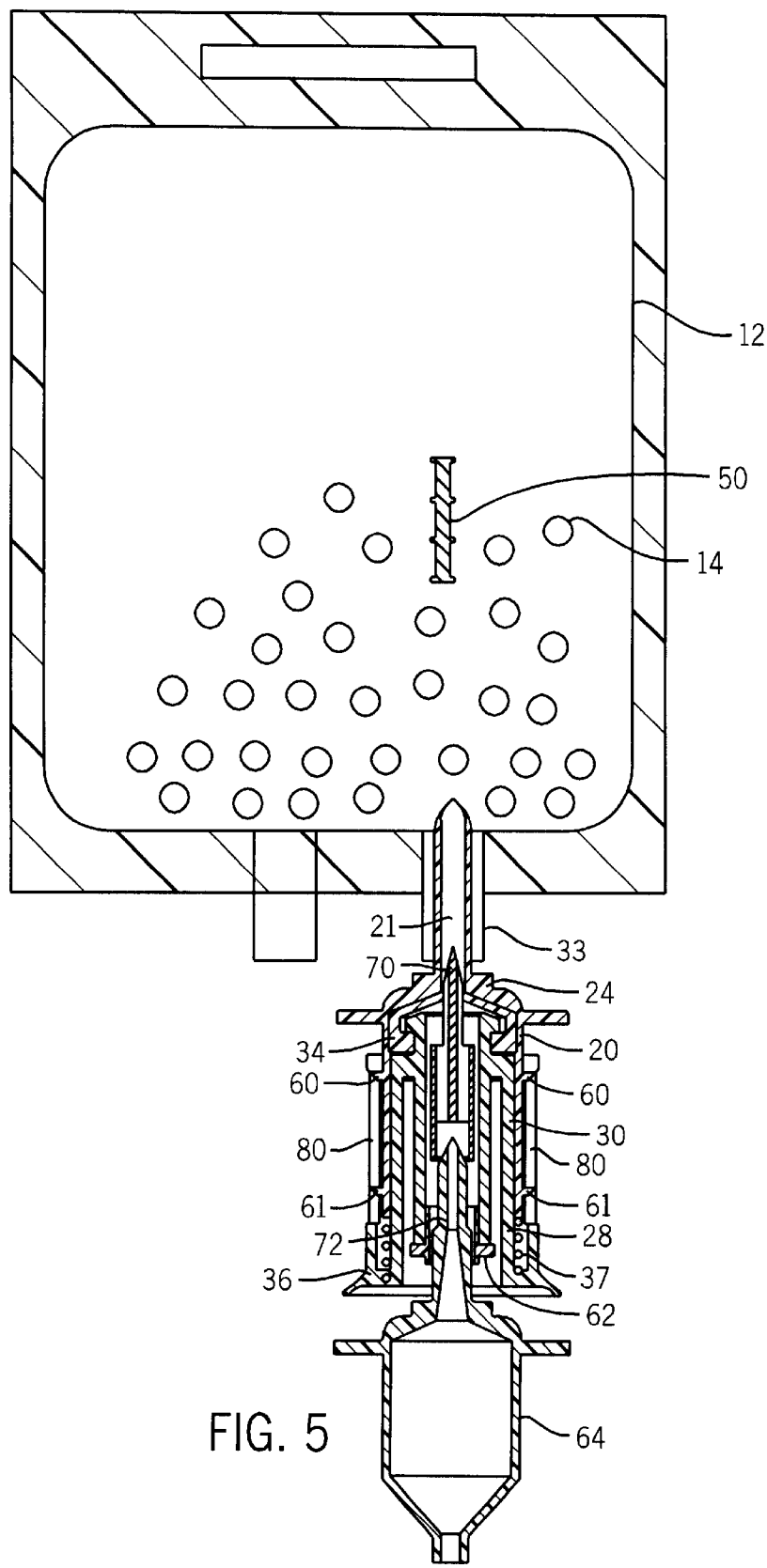
FIG. 5 is a cross-sectional view of the drug delivery system activated and mated with a standard IV bag and administration set.
Figure 6:
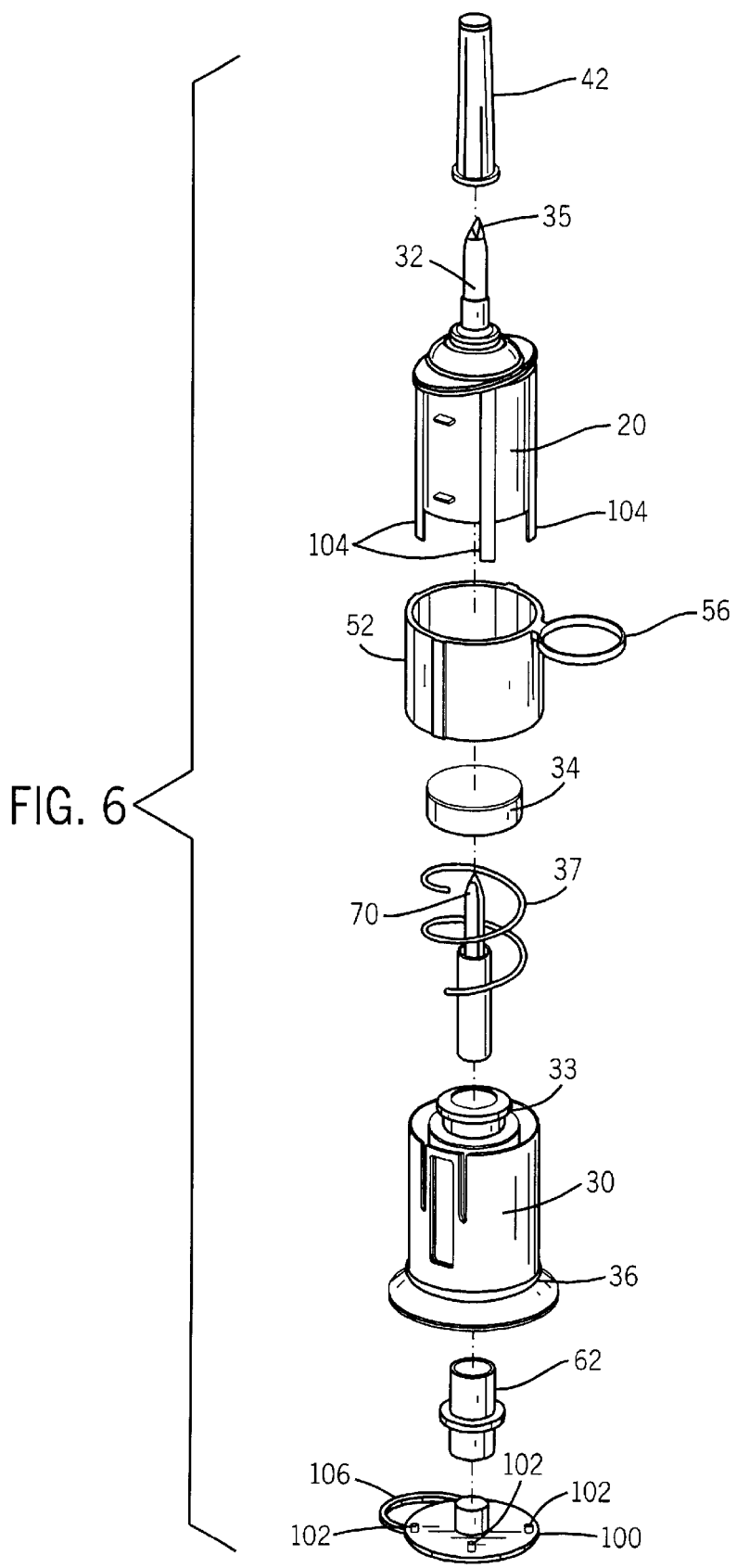
FIG. 6 is an exploded view of a preferred embodiment of the drug delivery system of the present invention with an alternative cover enclosing the access port.

Once the rubber plug 50 is removed from the delivery tube 32, the plunging action delivers the beneficial agent 14 from the container 20 through the delivery tube 32 and into the reservoir 12. The plunger 30 will not lock until substantially all the beneficial agent 14 is out of the drug chamber 38 (see FIG. 5). When the beneficial agent is in a powder or lyophilized form, the plunger 30 may have to be moved towards the second end 28 of the container 20 to repeat the plunging action. This involves hydrating the drug 14, which is accomplished with the assistance of the spring 37 biasing the plunger 30 away from the first end 24 of the container 20. Once all the beneficial agent 14 has been delivered to the reservoir 12 the upper tabs 60 of the lock will automatically engage with the slot 80 (see FIGS. 2B & 5). At this point, two visual features indicate that the drug delivery system has been activated. One visual feature is the presence of the rubber plug 50 in the reservoir 12. The other visual feature is the plunger 30 in the locked position.

The beneficial agent 14 and the diluent may be mixed further if necessary by shaking the reservoir 12. After mixing, the sterile seal 66 should be removed, revealing the access port 62. Then the second spike 72 on the administration set 64 should be inserted into the access port 62, pushing the penetrator 70 through the pierceable member 74 and creating a second flow path 75 between the reservoir 12 and the administration set 64. The location of the embedded penetrator 70 is a safety feature providing evidence if someone has previously accessed the drug delivery system. After connection of the beneficial agent delivery system 10 to the standard set 64 standard procedures of priming and administering the drug should be followed. The present drug delivery system need not be connected to-directly to a standard administration set, instead, the delivery system could be connected to a pump, burrette, or other device used to deliver a beneficial agent to a patient.

Although, the present drug delivery system has been described using a reservoir containing a fluid such as a diluent to be mixed with a beneficial agent delivered by the drug delivery system, it is understood that the component in the reservoir could include a beneficial agent with the delivery system containing and delivering to the reservoir a diluent.

The present drug delivery system may be used with a primary IV bag where the drug is mixed with the corresponding diluent and then delivered to the patient. Alternatively, the present drug delivery system could be used with a secondary reservoir where the drug is mixed with diluent and then delivered to an IV line with a primary reservoir. The flow rate of the beneficial agent and the diluent to the patient may be controlled using known procedures used by administrators of beneficial agents using a roller clamp, pump, burrette, or other means. Activation of the present drug delivery system may occur at the pharmacy or at the point of care.

Figure 7A:
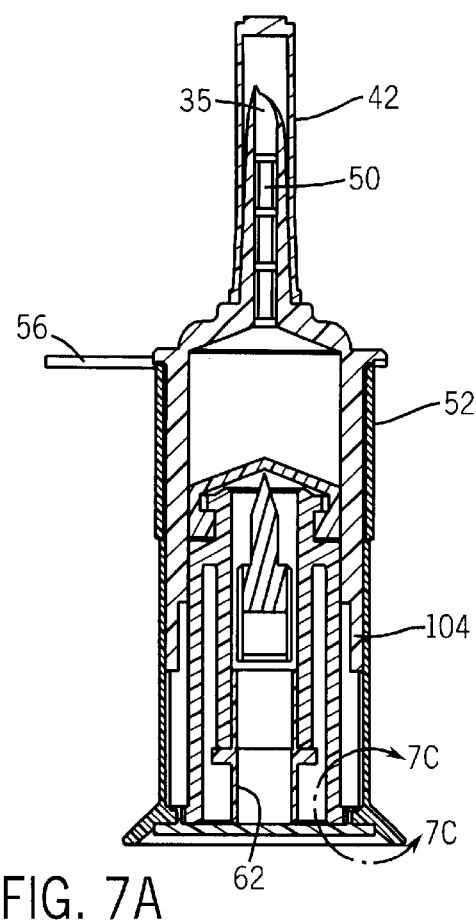
FIG. 7A is a cross-sectional view of the drug delivery system illustrated in FIG. 6 before the system is activated.
Figure 7B:
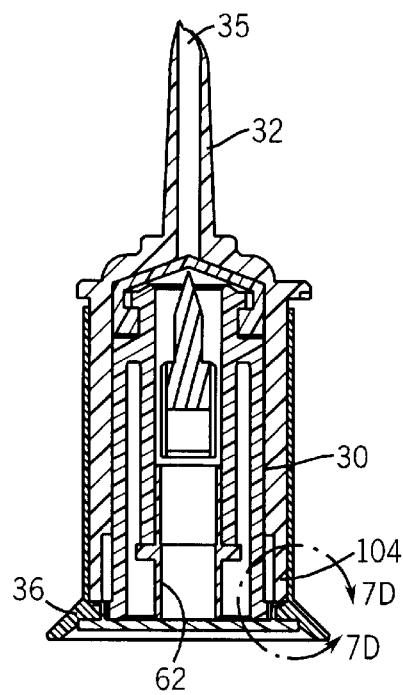
FIG. 7B is a cross-sectional view of the drug delivery system illustrated in FIG. 6 after the system is activated.
Figure 7C:
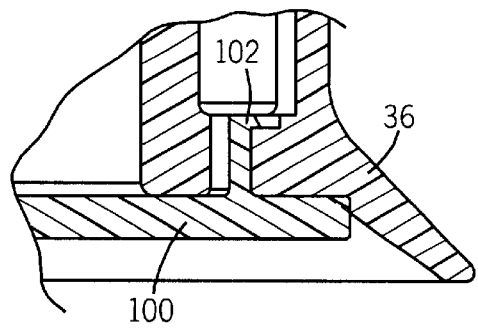
FIG. 7C is an enlarged, detailed view of portion 7C of the drug delivery system illustrated in FIG. 7A.
Figure 7D:
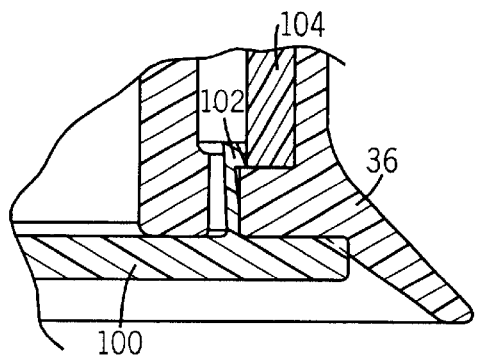
FIG. 7D is an enlarged, detailed view of portion 7D of the drug delivery system illustrated in FIG. 7B.

As shown in FIGS. 6, 7A, 7B, 7C, and 7D, a cover 100 enclosing the access port 62 may be added to the present drug delivery device to prevent the inadvertent spiking of the access port 62 prior to the delivery of substantially all the beneficial agent to the reservoir 12. The cover 100 may be used as an alternative to the seal 66 as shown in FIG. 4. The cover 100 has fasteners 102 that connect the cover 100 to the base 36 of the plunger member 30 as shown in FIGS. 7A and 7C prior to removal of the safety ring 56. When the plunger 30 has delivered substantially all the beneficial agent 14 to the reservoir 12, fingers 104 extending from the second end 28 of the container 20 push the fasteners 102 inward and away from the plunger 30 (see FIGS. 7B and 7D). At this point, the cover 100 may be removed by pulling on a cover tab 106, allowing access to the access port 62.

FIG. 8 shows another preferred embodiment of the present drug delivery system, comprising a flexible container 120. The flexible container 120 comprises a first end 124 having a delivery tube 32 and a second end 128. In this embodiment, no plunger is required to deliver the beneficial agent to the reservoir. Instead, the beneficial agent is delivered to the reservoir by contracting and expanding the container 120. The resulting drug and component mixture flows from the reservoir 12 into the container 120 to an access port 162.

A further embodiment of the present drug delivery system is shown in FIG. 9 comprising a collapsible container 220. In this further embodiment, the beneficial agent 14 is delivered to the reservoir 12 by squeezing the collapsible container 220 and forcing the beneficial agent 14 out of the container 220. After the beneficial agent 14 is mixed with the component in the reservoir 12, an administration set is attached to an access port 262 allowing the mixed beneficial agent and component to flow through the container 220 into the administration set 64.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art.

What is claimed is:

1. A drug delivery device for storing a beneficial agent and mixing the beneficial agent with a component in a reservoir, the drug delivery device comprising:

a container defining an interior space, the container having a first end portion, and a second end portion;

a first flow path providing fluid communication between the interior space of the container and a reservoir;

a plunger member for delivering the beneficial agent through the first flow path to a reservoir wherein the plunger includes a piston member that slides within the container; and an access port in fluid communication with a reservoir, wherein the mixed beneficial agent and component flow from a reservoir to the access port.

2. The drug delivery device of claim 1, further comprising a plug receivable within the first flow path, wherein the plug must be removed to establish fluid communication between the interior space of the container and a reservoir.

3. The drug delivery device of claim 1 wherein the plunger member has a first end portion and a second end portion, the first end portion of the plunger member and the first end portion of the container define a chamber for the beneficial agent, the first end portion of the plunger mounted within the interior of the container for plunging the beneficial agent through the first flow path to a reservoir.

4. The drug delivery device of claim 3, wherein the access port is mounted on the second end portion of the plunger member and the plunger member defines a second flow path therethrough from said first end portion to said second end portion, the second flow path providing fluid communication between a reservoir and the access port.

5. The drug delivery device of claim 4, further comprising a penetrator located within the plunger member, the plunger member having a pierceable member on the first end portion of the plunger for sealing fluid communication from a reservoir to the second flow path, wherein the penetrator pierces the pierceable member to establish fluid communication between a reservoir and the second flow path.

6. The drug delivery device of claim 3 further comprising a lock that engages the plunger member upon delivery of substantially all the beneficial agent to a reservoir.

7. The drug delivery device of claim 3, further comprising a safety ring attached to the container, wherein the safety ring prevents the first end portion of the plunger member from plunging towards the first end portion of the container.

8. The drug delivery device of claim 1 further comprising a cover for enclosing the access port, the cover having a fastener connected to the plunger member, wherein the the-container disconnects the fastener from the plunger member upon delivery of substantially all the beneficial agent to a reservoir.

9. The drug delivery device of claim 1 wherein the container is collapsible.

10. A drug delivery device comprising:
   a container defining an interior space, said container having a first end and a second end;
   a drug delivery tube extending from said first end of said container, said drug delivery tube defining a first flow path, said first flow path providing fluid communication between said interior space defined by said container and an external environment of said container;
   a plunger member having a first end portion and a second end portion, said first end portion of said plunger member mounted within said interior space defined by said container, said plunger member defining a second flow path therethrough from said first end portion to said second end portion of said plunger member, wherein the plunger includes a piston member that slides within the container; and
   an access port mounted on said second end of said plunger member, said access port defining a fluid flow channel therethrough in fluid communication with the second flow path.

11. The drug delivery device of claim 10 further comprising a plug within the first flow path, wherein the plug must be removed to establish fluid communication between the interior space and an external environment.

12. The drug delivery device of claim 10 further comprising a penetrator located within the plunger member, the plunger member having a pierceable member on the first end portion of the plunger member, wherein the penetrator pierces the pierceable member to provide fluid communication between the delivery tube and the second flow path.

13. A method of combining a beneficial agent with a component to form a mixture for administration thereof, comprising the steps of:
   a) providing a reservoir containing a component;
   b) providing a container defining an interior containing a beneficial agent, the container having a first end portion and a second end portion;
   c) establishing fluid communication between the interior of the container and the reservoir;
   c') providing a plunger with a piston member;
   c") sliding the piston member within the container;
   d) plunging the beneficial agent to the reservoir;
   e) mixing the component and the beneficial agent in the reservoir; and
   f) delivering the mixed beneficial agent and component through the container to an access port.

14. The method of combining a beneficial agent with a component to form a mixture for administration thereof of claim 13 further comprising the steps of providing an audible signal indicating that fluid communication between the reservoir and the container has been established.

15. The method of combining a beneficial agent with a component to form a mixture for administration thereof of claim 13 wherein the step of establishing fluid communication between the container and the reservoir includes the steps of:
   providing a drug delivery tube connected to the first end portion of the container with a plug fitted within the drug delivery tube, the plug preventing fluid communication between the reservoir and the container; and
   removing the plug from the delivery tube.

16. The method of combining a beneficial agent with a component to form a mixture for administration thereof of claim 15 wherein the step of establishing fluid communication between the container and the reservoir further includes the step of piercing a pierceable member of the reservoir.

17. The method of combining a beneficial agent with a component to form a mixture for administration thereof of claim 13, wherein the step of plunging the beneficial agent to the reservoir includes the steps of:
   providing a plunger member having a first end portion and a second end portion, the first end portion of the plunger member and the first end portion of the container define a chamber for the beneficial agent;
   moving the first end portion of the plunger member towards the first end portion of the container to plunge the beneficial agent from the chamber to the reservoir.

18. The method of combining a beneficial agent with a component to form a mixture for administration thereof of claim 17 wherein the step of delivering the mixed beneficial agent and component to an access port includes piercing a pierceable member of the plunger member to provide fluid communication between the reservoir and the access port.

19. The method of combining a beneficial agent with a component to form a mixture for administration thereof of claim 17 wherein the container includes a lock that engages the plunger member upon delivery of substantially all the beneficial agent to the reservoir.

20. A drug delivery device for storing a beneficial agent and mixing the beneficial agent with a component in a reservoir, the drug delivery device comprising:
   a container defining an interior space, the container having a first end portion, and a second end portion;
   a first flow path providing fluid communication between the interior space of the container and a reservoir;
   means for delivering the beneficial agent through the first flow path to a reservoir;
   an access port in fluid communication with a reservoir, wherein the mixed beneficial agent and component flow from a reservoir to the access port; and
   a cover for enclosing the access port, wherein the cover may not be removed from the drug delivery device before delivery of substantially all the beneficial agent to a reservoir.

* * * * *

UNITED STATES PATENT AND TRADEMARK OFFICE
CERTIFICATE OF CORRECTION

PATENT NO. : 6,685,692 B2
DATED : February 3, 2004
INVENTOR(S) : Marwan A. Fathallah It is certified that error appears in the above-identified patent and that said Letters Patent is hereby corrected as shown below:

Column 7,
Line 13, delete "the-"

Signed and Sealed this

Twenty-eighth Day of June, 2005

JON W. DUDAS
*Director of the United States Patent and Trademark Office*